(12) United States Patent
Iida et al.

(10) Patent No.: US 6,274,714 B1
(45) Date of Patent: Aug. 14, 2001

(54) METHOD FOR PRODUCING 1,2-NAPHTHOQUINONE-2-DIAZIDE-4-SULFONYL CHLORIDE

(75) Inventors: Hirotada Iida, Nakano-Ku; Seiju Tobishima, Yotsukaido; Naoki Sato, Chiba; Nobuhiro Yoneyama, Soka; Yuki Hotta; Toshio Itahana, both of Edogawa-Ku; Yuichi Hagiwara, Inba-Gun, all of (JP)

(73) Assignee: Toyo Gosei Kogyo Co., Ltd., Chiba (JP)

( * ) Notice: Subject to any disclaimer, the term of this patent is extended or adjusted under 35 U.S.C. 154(b) by 0 days.

(21) Appl. No.: 09/546,741

(22) Filed: Apr. 11, 2000

(30) Foreign Application Priority Data

Apr. 15, 1999 (JP) .................................... 11-107843

(51) Int. Cl.$^7$ .................................................. C07C 303/02
(52) U.S. Cl. ............................................................ 534/557
(58) Field of Search ............................................. 534/557

(56) References Cited

FOREIGN PATENT DOCUMENTS

| 269846 | * | 7/1989 | (DE) | ..................................... 534/557 |
| 59-196860 | | 11/1984 | (JP) . | |
| 8-27098 | | 1/1996 | (JP) . | |

OTHER PUBLICATIONS

Wolter et al., Chemical Abstracts, 112:178384, 1990.*

* cited by examiner

*Primary Examiner*—Fiona T. Powers
(74) *Attorney, Agent, or Firm*—Huntley & Associates

(57) ABSTRACT

An effective method for producing 1,2-naphthoquinone-2-diazide-4-sulfonyl chloride at high yield, wherein formation of impurities is prevented. The method includes the following steps: 1,2-naphthoquinone-2-diazide is reacted with chlorosulfuric acid, to thereby produce a mixture of a sulfonated compound and a chlorosulfonated compound of the diazide; and to the mixture, at least one substance selected from among thionyl chloride and phosphorus pentachloride is added for further reaction, to thereby obtain 1,2-naphthoquinone-2-diazide-4-sulfonyl chloride.

5 Claims, 2 Drawing Sheets

METHOD FOR PRODUCING 1,2-NAPHTHOQUINONE-2-DIAZIDE-4-SULFONYL CHLORIDE

BACKGROUND OF THE INVENTION

1. Field of the Invention

The present invention relates to a method for producing 1,2-naphthoquinone-2-diazide-4-sulfonyl chloride, which is an important starting material for preparing a radiation-sensitive positive photoresist composition, a photosensitive component of a positive photosensitive lithographic printing master plate, etc.

2. Background Art 1,2-Naphthoquinone-2-diazide-4-sulfonyl chloride has a chemical structure represented by the following formula (1). This compound has a melting point of 146–148° C. (decomposition). In "Chemical Abstracts," an abstract journal issued by the American Chemical Society, this compound is called 3-diazo-3,4-dihydro-4-oxo-1-naphthalenesulfonyl chloride, and the CAS registry number of the compound is "36451-09-9."

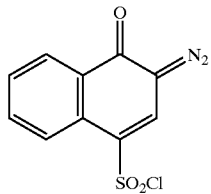

(1)

Methods for producing 1,2-naphthoquinone-2-diazide-4-sulfonyl chloride are divided into the following two types, (a) and (b), on the basis of the sequence of steps. Methods of type (a) are industrially employed at the present time. However, since methods of this type are not necessarily directly related to the method of the present invention, they will be briefly described only in outline form. Methods of type (b) are not industrially employed at the present time. However, since the method of the present invention is categorized under method (b), essential points of a typical known method categorized under method (b) will be described.

Methods of type (a) are drawn to a process in which sodium 1,2-naphthoquinone-2-diazide-4-sulfonate (CAS registry number: 64173-96-2) is synthesized (first step) and then converted to a compound of the above-described formula (1) (second step) (see, for example, DRP171024, DRP175593, German Patent Nos. 246573 and 246574, Japanese Patent Application Laid-Open (kokai) No. 196860/1984, and Japanese Patent Application Laid-Open (kokai) No. 27098/1996). According to such a method, many difficulties are encountered in the first step; i.e., in the synthesis of the compound of CAS registry number 64173-96-2. Particularly, synthesis of this compound is carried out by diazotization of sodium 3-amino-4-hydroxynaphthalene-1-sulfonate in the presence of a salt of a heavy metal such as copper, and therefore, the product is contaminated with a heavy metal salt. Thus, in order to make the compound usable as a photosensitizer for use in photoresist, the heavy metals must be eliminated. Practicing the elimination process for heavy metals on an industrial scale is considerably burdensome, and hence demand remains for a more effective method for producing the compound of formula (1).

Methods of type (b) are drawn to a process in which 1,2-naphthoquinone-2-diazide is treated with chlorosulfuric acid and thionyl chloride, to thereby yield the compound represented by formula (1). The method of the present invention is a method of this type. According to "Chemical Abstracts," 1,2-naphthoquinone-2-diazide is named 2-diazo-1(2H)-naphthalenone, and the CAS registry number of the compound is 879-15-2. The compound has a chemical structure represented by the following formula (2).

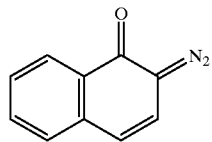

(2)

Methods of type (b) are industrially promising, but thus far there have been disclosed very few study examples thereof. The main reason is failure to establish effective methods for producing the compound represented by the above-described formula (2). The present inventors previously invented a significantly effective method for producing the compound described below (Japanese Patent Application No. 166744/1998). They continued studies on methods of type (b) in great detail, to thereby complete the present invention.

Very few published documents mention methods of type (b). E. Sauer et al. disclose a method in which 1,2-naphthoquinone-2-diazide is reacted with chlorosulfuric acid at 63° C. for 80 minutes, to thereby obtain a mixture of a sulfonated compound and a chlorosulfonated compound of the diazide. In this method, the theoretical yields of 1,2-naphthoquinone-2-diazide-4-sulfonic acid and 1,2-naphthoquinone-2-diazide-4-sulfonyl chloride are about 45% and about 50% respectively (J. Prakt. Chem. 333, 467 (1991)). B. I. Below et al. disclose a method in which 1,2-naphthoquinone-2-diazide is reacted in chlorosulfuric acid (14.3 times (by mol) the amount of the diazide) at 70° C. for two hours to thereby obtain crystals having a melting point of 138–139° C., and 1,2-naphthoquinone-2-diazide-5-sulfonyl chloride is obtained at a yield of 70% (U.S.S.R Pat. 173,756 (1964)). However, judging from the melting point of the crystals and the results of an experiment conducted by E. Sauer et al., the crystals are believed to be a mixture of the compound represented by formula (1), which serves as a main component, and 1,2-naphthoquinone-2-diazide-5-sulfonyl chloride. In addition, Wolter, Gerhard, et al. disclose a method in which 1,2-naphthoquinone-2-diazide is treated with a mixture of chlorosulfuric acid and thionyl chloride, to thereby obtain 1,2-naphthoquinone-2-diazide-4-sulfonyl chloride at a favorable yield (Ger. (East) Pat. DD 269,846 (1989)). The method disclosed by Wolter, Gerhard, et al. is outlined as follows.

A mixture consisting of 6–10 mol of chlorosulfuric acid and 2–5 mol of thionyl chloride based on 1 mol of 1,2-naphthoquinone-2-diazide is cooled, and crystals of 1,2-naphthoquinone-2-diazide are added thereto portionwise. The mixture is reacted at 35–60° C. for 1–3 hours, cooled to room temperature, and poured into a mixture of water and ice. The precipitated crude product is separated and purified through crystallization from acetone at a temperature between −5° C. and −10° C. inclusive. 1,2-Naphthoquinone-2-diazide-4-sulfonyl chloride is described as having a theoretical yield of 70–75%.

The present inventors considered the aforementioned methods of type (b), in which 1,2-naphthoquinone-2-diazide is used as a starting material, to be promising for industrial production of 1,2-naphthoquinone-2-diazide-4-sulfonyl chloride, and re-examined a method disclosed in the aforementioned DD 269,846, which is the sole known document mentioning the above method. As a result, the inventors have found that such problems as (1), (2), and (3) described below remain unsolved and that solution of the problems is outstanding.

(1) Problems Involved in Reaction with Thionyl Chloride

In the method disclosed in DD 269,846, 1,2-naphthoquinone-2-diazide is added to a mixture of chlorosulfuric acid and thionyl chloride, and the resultant mixture is allowed to react. However, after studying the method the present inventors have found that the method is unfavorable in the following ways. Crude crystals obtained by treating 1,2-naphthoquinone-2-diazide with a mixture of chlorosulfuric acid and thionyl chloride in accordance with the Example disclosed in DD 269,846 exhibit strong color, the yield of the target compound is poor, and the target compound contains many kinds of impurities. Chlorosulfonation of an aromatic compound making use of a mixture of chlorosulfuric acid and thionyl chloride is generally and widely employed. For example, Blank, Heinz Ulrich discloses a method in which benzene is treated with a mixture of chlorosulfuric acid and thionyl chloride at 50° C. for four hours, to thereby obtain benzenesulfonyl chloride at high purity (Ger. Offen, 2,635,279 (1978)). Sasaki et al. disclose a method in which sodium 1,2-naphthoquinone-2-diazide-4-sulfonic acid is treated with a mixture of chlorosulfuric acid and thionyl chloride at 70° C. for eight hours, to thereby obtain 1,2-naphthoquinone-2-diazide-4-sulfonyl chloride at a yield of 80% (Japanese Patent Application Laid-Open (kokai) No. 27098/1996). Thus, a mixture of chlorosulfuric acid and thionyl chloride is excellent for use as a chlorosulfonation agent for an aromatic compound. However, the present inventors have unexpectedly found that the mixture cannot favorably be applied to 1,2-naphthoquinone-2-diazide. The present inventors have extensively studied the reactivity of 1,2-naphthoquinone-2-diazide and found that, surprisingly, the diazide reacts quite well with thionyl chloride itself at room temperature and produces a mixture of many kinds of species. Also, through analysis by means of liquid chromatography, the mixture produced is identical to impurities other than 1,2-naphthoquinone-2-diazide-4-sulfonyl chloride contained in crystals produced in accordance with the method disclosed in DD 269,846. Furthermore, an experiment carried out by the present inventors clarified that the mixture produced through reaction of 1,2-naphthoquinone-2-diazide with thionyl chloride is thermally unstable and decomposes explosively at about 110° C. Because, as described previously, the target compound, 1,2-naphthoquinone-2-diazide-4-sulfonyl chloride, has a decomposed temperature of 146–148° C. and decomposes explosively at that temperature, the industrial product should not be contaminated with impurities which decompose explosively at 110° C. Accordingly, using a mixture of chlorosulfuric acid and thionyl chloride as a chlorosufoniation agent for 1,2-naphthoquinone-2-diazide is inappropriate, and a new method must be developed.

With regard to a reaction mechanism by which 1,2-naphthoquinone-2-diazide and thionyl chloride react and a mixture containing a variety of species is produced, the present inventors understand the following. Upon application of heat thionyl chloride is known to produce decomposed products of the following formula (3) (P. W. Schenk, H. Tribel, Z. Anorg. Allg. Chem. 229 (1936), 305).

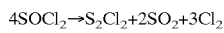

$$4SOCl_2 \rightarrow S_2Cl_2 + 2SO_2 + 3Cl_2 \qquad (3)$$

Also, in the reaction of 1,2-naphthoquinone-2-diazide with thionyl chloride such decomposed products are produced from thionyl chloride. It seems that the decomposed products, particularly chlorine, react with 1,2-naphthoquinone-2-diazide, to thereby produce impurities. In the aforementioned method disclosed by Sasaki et al. (Japanese Patent Application Laid-Open (kokai) No. 27098/1996), 1,2-naphthoquinone-2-diazide-4-sulfonyl chloride is obtained at an excellent yield. The reason for this is understood to be that the sodium 1,2-naphthoquinone-2-diazide-4-sulfonate employed by Sasaki et al. as a starting material does not easily react with the aforementioned decomposed products, such as thionyl chloride.

(2) Problems Regarding Thermal Instability of 1,2-Naphthoquinone-2-diazide 1,2-Naphthoquinone-2-diazide is thermally unstable, and treating a large amount of solid diazide on an industrial scale has been considered dangerous. FIG. 1 shows a DSC (differential scanning calorimetry) curve of 1,2-naphthoquinone-2-diazide crystals(recrystalized from toluene). As shown in FIG. 1, the crystals melt at 77.3° C., begin to decompose at about 95° C., and the exothermic decomposition reaches a peak at 128.2° C. Although 1,2-naphthoquinone-2-diazide is thermally unstable and therefore a dangerous crystalline substance, experiments described in all the disclosed documents mentioning sulfonation or chlorosulfonation of 1,2-naphthoquinone-2-diazide employ solid 1,2-naphthoquinone-2-diazide. Industrial treatment of such a thermally unstable compound in a solid state is unsuitable, and establishment of a safer method for treating the compound is of great interest.

When 1,2-naphthoquinone-2-diazide is prepared in accordance with a method (3) described below, the filtered solid contains water in an amount of 100–150% the target pure product. In order to react 1,2-naphthoquinone-2-diazide with chlorosulforic acid or thionyl chloride water must be completely eliminated. However, elimination of water from a solid substance is difficult, requiring warm air-drying at 40–50° C. for about ten hours and further drying under reduced pressure at 40° C. Also, in such a drying process, solid 1,2-naphthoquinone-2-diazide may thermally decompose, thus involving danger.

(3) Problems in Preparation of 1,2-Naphthoquinone-2-diazide

Three or four documents disclose an experimental method for preparing 1,2-naphthoquinone-2-diazide, which serves as a starting material for 1,2-naphthoquinone-2-diazide-4-sulfonyl chloride, but no suitable method for producing the compound on an industrial scale has yet been disclosed. Patent DD 269,846 recommends the method disclosed in another patent by Wolter, Gerhard, et al. (Ger. (East Germany) DD 221,174 (1984)) as a method for producing 1,2-naphthoquinone-2-diazide which serves as a starting material. However, in this method the yield of 1,2-naphthoquinone-2-diazide from 2-amino-1-naphthalenesulfonic acid is as low as 63%, making this method unsuitable for industrial-scale production.

SUMMARY OF THE INVENTION

In view of the foregoing, an object of the present invention is to provide a method for producing 1,2-naphthoquinone-2-diazide-4-sulfonyl chloride at high yield, while preventing formation of impurities.

The present invention solves the aforementioned problems and is drawn to a method for producing 1,2-naphthoquinone-2-diazide-4-sulfonyl chloride, wherein 1,2-naphthoquinone-2-diazide is reacted with chlorosulfuric acid to thereby produce a mixture of a sulfonated compound and a chlorosulfonated compound of the diazide; and at least one substance selected from among thionyl chloride and phosphorus pentachloride is added to the mixture for further reaction, to thereby obtain 1,2-naphthoquinone-2-diazide-4-sulfonyl chloride.

Preferably, conditions for the aforementioned reaction between 1,2-naphthoquinone-2-diazide and chlorosulfuric acid are such that 80% or more of 1,2-naphthoquinone-2-diazide is consumed by the reaction.

Also preferably, the aforementioned chlorosulfuric acid is mixed with a diazide solution which has been prepared by dissolving the aforementioned 1,2-naphthoquinone-2-diazide in an organic solvent which is inert to chlorosulfuric acid, and the aforementioned reaction between 1,2-naphthoquinone-2-diazide and chlorosulfuric acid is carried out in the presence of the organic solvent or under a condition that the organic solvent has been eliminated.

Preferably, the aforementioned diazide solution is a solution which is prepared by treating 2-diazo-1-naphthalenesulfonic acid in an aqueous alkaline solution containing an oxidizer and iodide ions, to thereby obtain an aqueous dispersion of 1,2-naphthoquinone-2-diazide, and extracting 1,2-naphthoquinone-2-diazide by use of an alkyl chloride.

In the present invention, specifically, 5–10 mol of chlorosulfuric acid is mixed per 1 mol of the aforementioned 1,2-naphthoquinone-2-diazide, and the resultant mixture is reacted at 40–70° C. for 1–4 hours, to thereby produce a mixture of a sulfonated compound and a chlorosulfonated compound of the aforementioned 1,2-naphthoquinone-2-diazide from the diazide.

Next, to a reaction mixture of 1,2-naphthoquinone-2-diazide and the aforementioned chlorosulfuric acid there is added at least one substance (0.8–5 mol) selected from among thionyl chloride and phosphorus pentachloride, and the resultant mixture is further reacted for 1–3 hours at 40–70° C.

The present invention has been attained on the basis of a finding that when the process for producing 1,2-naphthoquinone-2-diazide-4-sulfonyl chloride from 1,2-naphthoquinone-2-diazide is conducted in a two-step reaction the process produces a target compound with few impurities. As mentioned in connection with problem (1), the reaction between 1,2-naphthoquinone-2-diazide and thionyl chloride yields impurities other than a target compound produced during the reaction of 1,2-naphthoquinone-2-diazide with a mixture of chlorosulforic acid and thionyl chloride. Thus, in order to prevent formation of such impurities 1,2-naphthoquinone-2-diazide and thionyl chloride are not allowed to coexist. The present invention has been accomplished on the basis of this finding.

In a first-step reaction of the present invention, under conditions which cause consumption—preferably 100% consumption—of 1,2-naphthoquinone-2-diazide, 1,2-naphthoquinone-2-diazide is allowed to react with chlorosulfuric acid, to thereby produce a mixture of 1,2-naphthoquinone-2-diazide-4-sulfonyl chloride and 1,2-naphthoquinone-2-diazide-4-sulfonic acid.

In a second-step reaction of the present invention, to the mixture obtained in the first-step reaction, thionyl chloride or phosphorus pentachloride is added for further reaction, to thereby convert residual 1,2-naphthoquinone-2-diazide-4-sulfonic acid to 1,2-naphthoquinone-2-diazide-4-sulfonyl chloride.

Ideally the second-step reaction is carried out after 100% of 1,2-naphthoquinone-2-diazide has been consumed in the first-step reaction of the present invention. However, a considerable reduction in the amount of impurities can be attained even when the second-step reaction starts after 1,2-naphthoquinone-2-diazide has been consumed in an amount of about 80%.

As mentioned in detail in connection with problem (2), 1,2-naphthoquinone-2-diazide is thermally unstable and moreover, a process for producing a solid and dried 1,2-naphthoquinone-2-diazide is likely to be dangerous. After conducting various experiments, the present inventors have found that the aforementioned problem (2) can be solved by the following method: in a process for producing 1,2-naphthoquinone-2-diazide-4-sulfonyl chloride, 1,2-naphthoquinone-2-diazide is treated not in solid form but in the form of a solution obtained by dissolution in an organic solvent which is inert to chlorosulfuric acid. That is, according to a preferred mode of the present invention for producing 1,2-naphthoquinone-2-diazide-4-sulfonyl chloride, 1,2-naphthoquinone-2-diazide is treated not in solid form but in the form of a solution obtained by dissolution in an organic solvent which is unreactive with chlorosulfuric acid.

Suitable examples of organic solvents which are stable with respect to chlorosulfuric acid include alkyl chlorides such as methylene chloride, chloroform, 1,2-dichloroethane, and 1,1,1-trichloroethane. Among them, methylene chloride is particularly suitable.

When 1,2-naphthoquinone-2-diazide is dissolved in 1,1,1-trichloroethane and chlorosulfuric acid is added dropwise to the solution, a large amount of yellow-brown solid precipitates, whereas when methylene chloride is used instead of 1,1,1-trichloroethane, precipitation of such a solid is unlikely. The solid is an initial reaction product between 1,2-naphthoquinone-2-diazide and chlorosulfuric acid, and appears to be a mixture of 1,2-naphthoquinone-2-diazide ($C_{10}H_6N_2O$) and acids ($H_2SO_4$, HCl, $ClSO_3H$). Results of chemical analysis carried out on the product correspond approximately to theoretical properties of a mixture containing $C_{10}H_6N_2O \cdot H_2SO_4$ and $C_{10}H_6N_2O \cdot ClSO_3H$ at a ratio of 2:1, as obtained through calculation. The yellow-brown solid is thermally more unstable than 1,2-naphthoquinone-2-diazide and thermally decomposes at 123° C. FIG. 2 shows the DSC curve of the product. Accordingly, selection of conditions under which such yellow-brown solids are not deposited is critical.

As mentioned in relation to problem (3), no known document discloses a method for producing a large amount of 1,2-naphthoquinone-2-diazide. The present inventors have extensively studied a synthesis method for the compound, and have invented an excellent industrial method (Japanese Patent Application No. 166744/1998). The following is an outline of that production method.

2-Amino-1-naphthalene sulfonic acid is diazotized, and a catalytic amount of iodide ions are added to the resultant alkaline solution. To the mixture an aqueous solution mixture of an oxidizer such as sodium hypochlorite and sodium hydroxide are added dropwise at 20° C. over 2–4 hours, and the resultant 1,2-naphthoquinone-2-diazide is isolated. Theoretical yield of the compound is 90–95%. According to the method of the present invention for producing 1,2-naphthoquinone-2-diazide-4-sulfonyl chloride, 1,2-naphthoquinone-2-diazide is treated not in solid form but in the form of a solution obtained by dissolution in an organic solvent which is inert with respect to chlorosulfuric acid. Accordingly, in the above-described method invented by the present inventors, preferably, 1,2-naphthoquinone-2-diazide is not isolated in solid form, but the dispersed 1,2- naphthoquinone-2-diazide in a reaction mixture containing water as a main component is extracted by means of an organic solvent which is inert to chlorosulfuric acid; and the solution is mixed, as is, with chlorosulfuric acid for further reaction.

BRIEF DESCRIPTION OF THE DRAWINGS

Various other objects, features, and many of the attendant advantages of the present invention will be readily appreciated as the same becomes better understood with reference to the following detailed descriptions of the preferred embodiments when considered in connection with the accompanying drawings, in which.

DETAILED DESCRIPTION OF PREFERRED EMBODIMENTS

Figure 1:
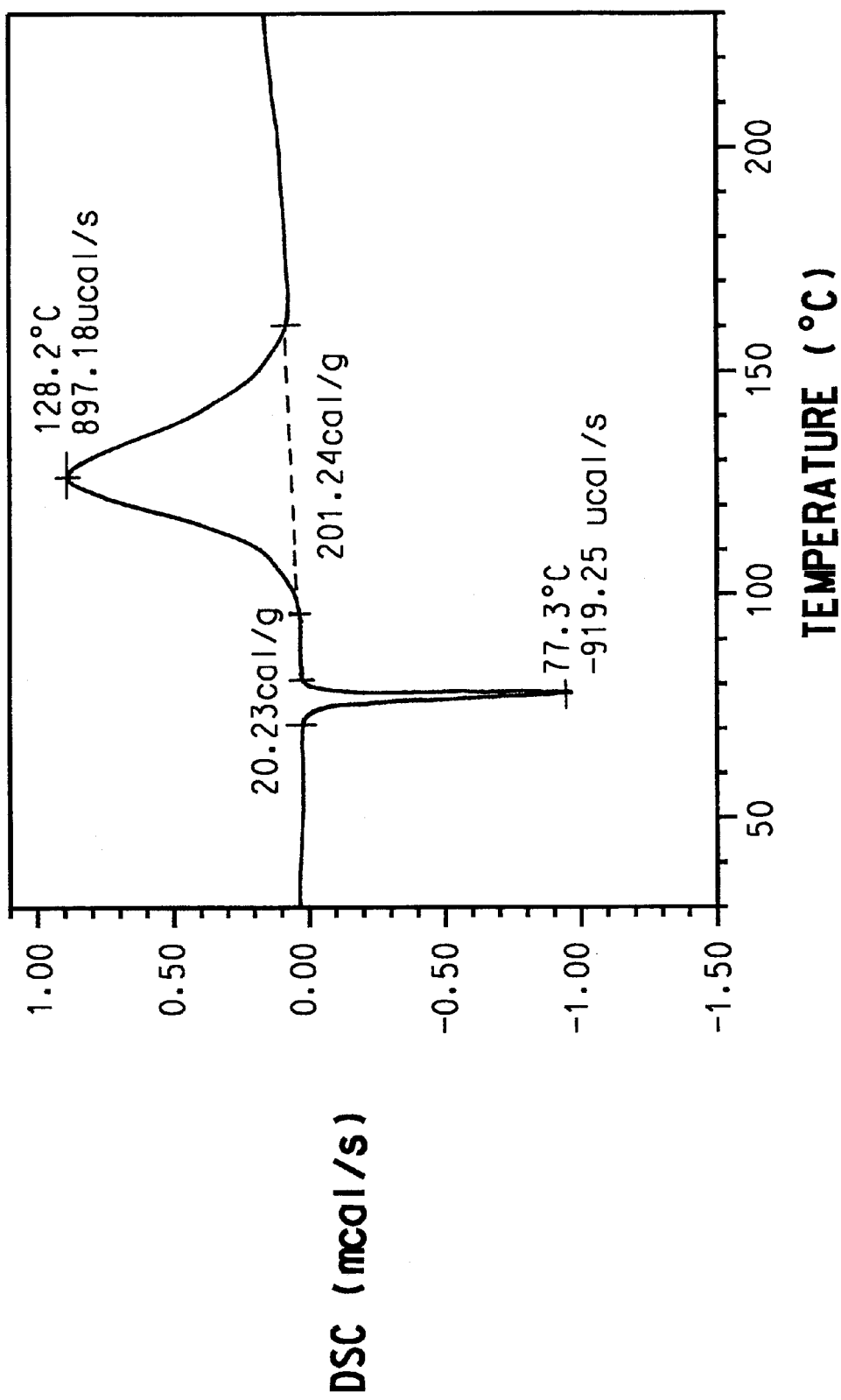
FIG. 1 is a graph showing a DSC curve of 1,2-naphthoquinone-2-diazide.
Figure 2:
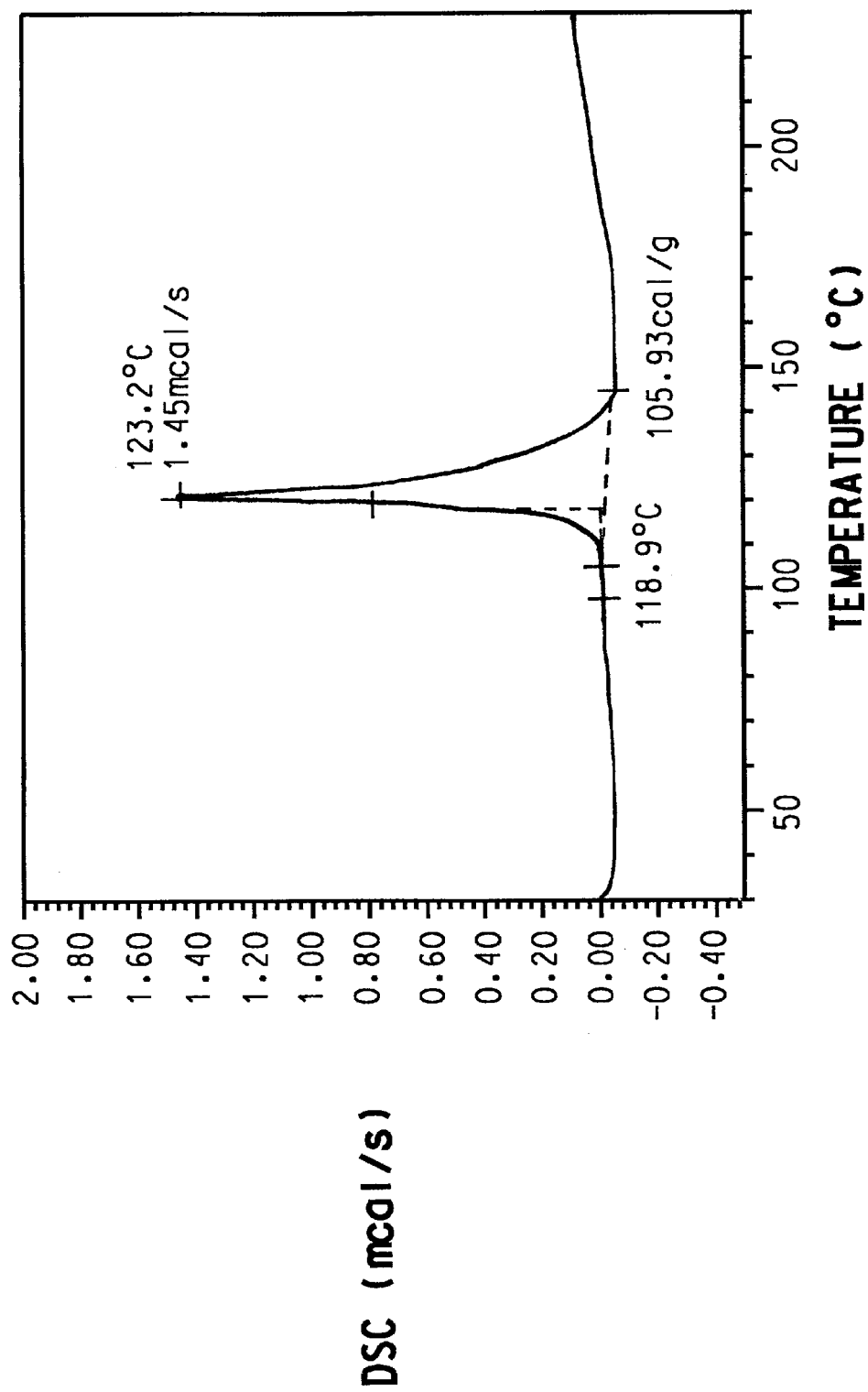
FIG. 2 is a graph showing a DSC curve of an initial reaction product between 1,2-naphthoquinone-2-diazide and chlorosulfuric acid.

The method of the present invention is drawn to a combination of steps, each having its own significance, and an outline of the method will next be described.

Outline of the Production Method

Preparation of an Alkyl Chloride Solution of 1,2-Naphthoquinone-2-diazide:

Sodium 2-amino-1-naphthalene sulfonate is diazotized in an aqueous solution, and a catalytic amount of potassium iodide is added thereto. Sodium hypochlorite and an aqueous solution of sodium hydroxide are added dropwise to the resultant solution, to thereby prepare an aqueous dispersion of 1,2-naphthoquinone-2-diazide. Alkyl chloride in an amount of 5–8 times (by weight) the diazide is added to the dispersion, and the resultant target diazide is extracted, followed by washing with water.

Chlorosulfonation Reaction:

Preferably, an alkyl chloride solution of 1,2-naphthoquinone-2-diazide and chlorosulfuric acid in an amount of 5–8 mol equivalents of the contained diazide are mixed, and reaction of the mixture is allowed to proceed for 1–4 hours at 45–70° C., preferably until 1,2-naphthoquinone-2-diazide is completely consumed. Subsequently, thionyl chloride in an amount of 0.8–5 mol equivalents of 1,2-naphthoquinone-2-diazide is added thereto, and the reaction is continued for 1–3 additional hours at 45–65° C. Isolation of 1,2-naphthoquinone-2-diazide-4-sulfonyl chloride:

The reaction mixture is poured into a mixture of water and ice, and a target compound is extracted by means of an organic solvent such as methylene chloride or benzene. The solvent is distilled off, and precipitated crystals of interest are separated by filtration and washed with an organic solvent such as hexane, followed by drying.

Hereinafter, the present invention will be described by way of examples, which should not be construed as limiting the invention thereto.

EXAMPLE 1

Diluted hydrochloric acid (850 g) containing 0.68 mol of hydrochloric acid was cooled to 5° C. Separately, sodium hydroxide (0.3 mol), 2-amino-1-naphthalenesulfonic acid (0.3 mol), and sodium nitrite (0.303 mol) were dissolved sequentially in water (700 g), and the solution was cooled to 5° C. The solution was added to the aforementioned diluted hydrochloric acid in a short time under vigorous agitation, followed by continuous agitation for 30 minutes. The resultant opaque solution of 2-diazo-1-naphthalenesulfonic acid was neutralized, and potassium iodide (3 g) was added thereto and dissolved. A mixture containing an aqueous solution of sodium hypochlorite (180 g; available chlorine 13.3%) and a 35% aqueous solution of sodium hydroxide (69 g) was added dropwise at 20–25° C. over 2–3 hours. After completion of the reaction, the reaction mixture was neutralized by addition of hydrochloric acid, and free iodine was removed therefrom by addition of sodium thiosulfate. The obtained 1,2-naphthoquinone-2-diazide was extracted by means of methylene chloride (200–300 g). The theoretical yield of 1,2-naphthoquinone-2-diazide is 95%.

From the methylene chloride solution of the thus-obtained 1,2-naphthoquinone-2-diazide, a portion of the solution containing 0.1 mol of 1,2-naphthoquinone-2-diazide was separated and subjected to azeotropic dehydration at ambient pressure. To the reaction mixture, chlorosulfuric acid (0.5 mol) was added dropwise over 30 minutes with stirring, while the liquid temperature was maintained at 10–15° C., to thereby obtain a homogeneous dark violet-black-colored solution. The solution was warmed to 50° C. while the methylene chloride was distilled off, and the solution was continuously stirred for 2.5 hours at the same temperature. A small amount of the reaction mixture was subjected to analysis by liquid chromatography. The results confirm that 1,2-naphthoquinone-2-diazide had completely reacted and was consumed in its entirety.

Subsequently, thionyl chloride (0.27 mol) was added dropwise to the mixture over 30 minutes at 50° C., followed by stirring for 2.5 hours at 50° C. After completion of the reaction, the reaction mixture was added dropwise over about 30 minutes to a mixture of water (250 g) and crushed ice (250 g). The precipitated matter was extracted with benzene (about 600 ml), washed with water, fractionated, and subsequently benzene was allowed to evaporate under reduced pressure, to thereby obtain 25.5 g of minute crystals. The compound was identified as 1,2-naphthoquinone-2-diazide-4-sulfonyl chloride of 95.0% purity, and the theoretical yield of the compound is 90%.

EXAMPLES 2 THROUGH 4

Examples 2 through 4 were carried out in a manner similar to that of Example 1, except that the mol ratios of chlorosulforic acid and thionyl chloride to 1,2-naphthoquinone-2-diazide were as shown in Table 1. The results are also presented in Table 1.

TABLE 1

| Example No. | Mol ratios of ClSO$_3$H and SOCl$_2$ to 1,2-naphthoquinone-2-diazide | | Yield of 1,2-naphthoquinone-2-diazide-4-sulfonyl chloride (%) |
|---|---|---|---|
| | ClSO$_3$H | SOCl$_2$ | |
| Example 2 | 5.0 | 1.5 | 89 |
| Example 3 | 5.0 | 0.8 | 66 |
| Example 4 | 8.0 | 2.7 | 82 |

EXAMPLES 5 AND 6

Examples 5–6 were carried out in a manner similar to that of Example 1, except that reaction temperatures were set as shown in Table 2. The results are also presented in Table 2.

TABLE 2

| Example No. | Reaction temperature (° C.) | Yield of 1,2-naphthoquinone-2-diazide-4-sulfonyl chloride (%) |
| --- | --- | --- |
| Example 5 | 70 | 85 |
| Example 6 | 60 | 87 |

EXAMPLE 7

The same procedure as that in Example 1 was repeated, except that thionyl chloride (0.1 mol) and phosphorus pentachloride (0.1 mol) were used instead of thionyl chloride (0.27 mol) in Example 1. 1,2-Naphthoquinone-2-diazide-4-sulfonyl chloride was obtained at a theoretical yield of 87%.

COMPARATIVE EXAMPLE 1

The same process as in Example 4 was repeated, except that dropwise addition of thionyl chloride was conducted at the same time as addition of chlorosulfuric acid, to thereby obtain a deep-black solid. The yield of 1,2-naphthoquinone-2-diazide-4-sulfonyl chloride was 61% with respect to the consumed 1,2-naphthoquinone-2-diazide.

COMPARATIVE EXAMPLE 2

The same process as in Example 1 was repeated, except that dropwise addition of thionyl chloride was conducted at the same time as addition of chlorosulforic acid, to thereby obtain an oily substance in which a great amount of raw material, 1,2-naphthoquinone-2-diazide, remained. The yield of 1,2-naphthoquinone-2-diazide-4-sulfonyl chloride was 35% with respect to the consumed 1,2-naphthoquinone-2-diazide.

What is claimed is:

1. A method for producing 1,2-naphthoquinone-2-diazide4-sulfonyl chloride comprising:

reacting 1,2-naphthoquinone-2-diazide with chlorosulfuric acid to thereby produce a mixture of a sulfonated compound and a chlorosufonated compound of the diazide; and adding at least one substance selected from among thionyl chloride and phosphorus pentachloride to the mixture for further reaction, to thereby obtain 1,2-naphthhoguinone-2-diazide-4-sulfonyl chloride, wherein conditions for the reaction between 1,2-naphthoquinone-2-diazide and chlorosulfuric acid are such that 80% or more of 1,2-naphthoquinone-2-diazide is consumed by the reaction.

2. A method for producing 1,2-naphthoquinone-2-diazide-4-sulfonyl chloride according to claim 1, wherein the chlorosulfuric acid is mixed with diazide solution which has been prepared by dissolving the 1,2-naphthoquinone-2-diazide in an organic solvent which is inert to chlorosulforic acid, and the reaction between 1,2-naphthoquinone-2-diazide and chlorosulfuric acid is carried out in the presence of the organic solvent or under a condition that the organic solvent has been eliminated.

3. A method for producing 1,2-naphthoquinone-2-diazide-4-sulfonyl chloride according to claim 2, wherein the diazide solution is a solution which is prepared by treating 2-diazo-1-naphthalenesulfonic acid in an aqueous alkaline solution containing an oxidizer and iodide ions, to thereby obtain an aqueous dispersion of 1,2-naphthoquinone-2-diazide, and extracting 1,2-naphthoquinone-2-diazide by use of an alkyl chloride.

4. A method for producing 1,2-naphthoquinone-2-diazide-4-sulfonyl chloride according to claim 1, wherein 5–10 mol of chlorosulfuric acid is mixed per 1 mol of 1,2-naphthoquinone-2-diazide, and the resultant mixture is reacted at 40–70° C. for 1–4 hours, to thereby produce a mixture of a sulfonated compound and a chlorosulfonated compound of the 1,2-naphthoquinone-2-diazide from the diazide.

5. A method for producing 1,2-naphthoquinone-2-diazide-4-sulfonyl chloride according to claim 4, wherein, to a reaction mixture of the 1,2-naphthoquinone-2-diazide and chlorosulfuric acid, 0.8–5 mol of at least one substance selected from among thionyl chloride and phosphorus pentachloride is added, and the resultant mixture is further reacted for 1–3 hours at 40–70° C.

* * * * *